(12) United States Patent
Jonda et al.

(10) Patent No.: US 6,513,364 B1
(45) Date of Patent: Feb. 4, 2003

(54) HYDROGEN SENSOR

(75) Inventors: Sven Jonda, Alxing (DE); Hans Meixner, Haar (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/674,190
(22) PCT Filed: Apr. 1, 1999
(86) PCT No.: PCT/DE99/01003
§ 371 (c)(1),
(2), (4) Date: Oct. 27, 2000
(87) PCT Pub. No.: WO99/57548
PCT Pub. Date: Nov. 11, 1999

(30) Foreign Application Priority Data

Apr. 30, 1998 (DE) .......................... 198 19 575

(51) Int. Cl.$^7$ .............................. G01N 7/00; H01C 7/00
(52) U.S. Cl. .......................................... 73/31.06; 338/34
(58) Field of Search ........................ 73/31.05, 31.06; 338/34

(56) References Cited

U.S. PATENT DOCUMENTS

| | | | | |
|---|---|---|---|---|
| 4,347,732 A | * | 9/1982 | Leary ..................... | 73/31.05 |
| 4,542,640 A | * | 9/1985 | Clifford .................. | 73/31.05 |
| 4,937,219 A | * | 6/1990 | Haruta et al. ............ | 502/174 |
| 5,618,496 A | * | 4/1997 | Hasumi et al. ........... | 73/31.06 |
| 5,783,154 A | * | 7/1998 | Althainz et al. ......... | 73/31.06 |
| 5,945,069 A | * | 8/1999 | Buehler .................. | 422/90 |
| 6,202,471 B1 | * | 3/2001 | Yadav et al. ............ | 73/31.05 |

FOREIGN PATENT DOCUMENTS

| | | | |
|---|---|---|---|
| DE | 42 03 522 C1 | 5/1993 | |
| DE | 43 39 737 C1 | 1/1995 | |
| EP | 0 603 945 A1 | 6/1994 | |
| EP | 0 798 554 A2 | 10/1997 | |
| JP | 03020659 A | * 1/1991 | ................ 73/31.05 |

* cited by examiner

Primary Examiner—Hezron Williams
Assistant Examiner—Michael Cygan
(74) Attorney, Agent, or Firm—Harness, Dickey & Pierce, P.L.C.

(57) ABSTRACT

A hydrogen sensor employs a hydrogen-sensitive semiconductor layer that is applied to a carrier substrate. The hydrogen-sensitive semiconductor layer includes a first and second semiconductor layers that consist of strontium titanate so as to compensate for temperature fluctuations in the hydrogen-sensitive semiconductor layer. The first and second semiconductor layers include a respective and different electrical conductivity.

14 Claims, 1 Drawing Sheet

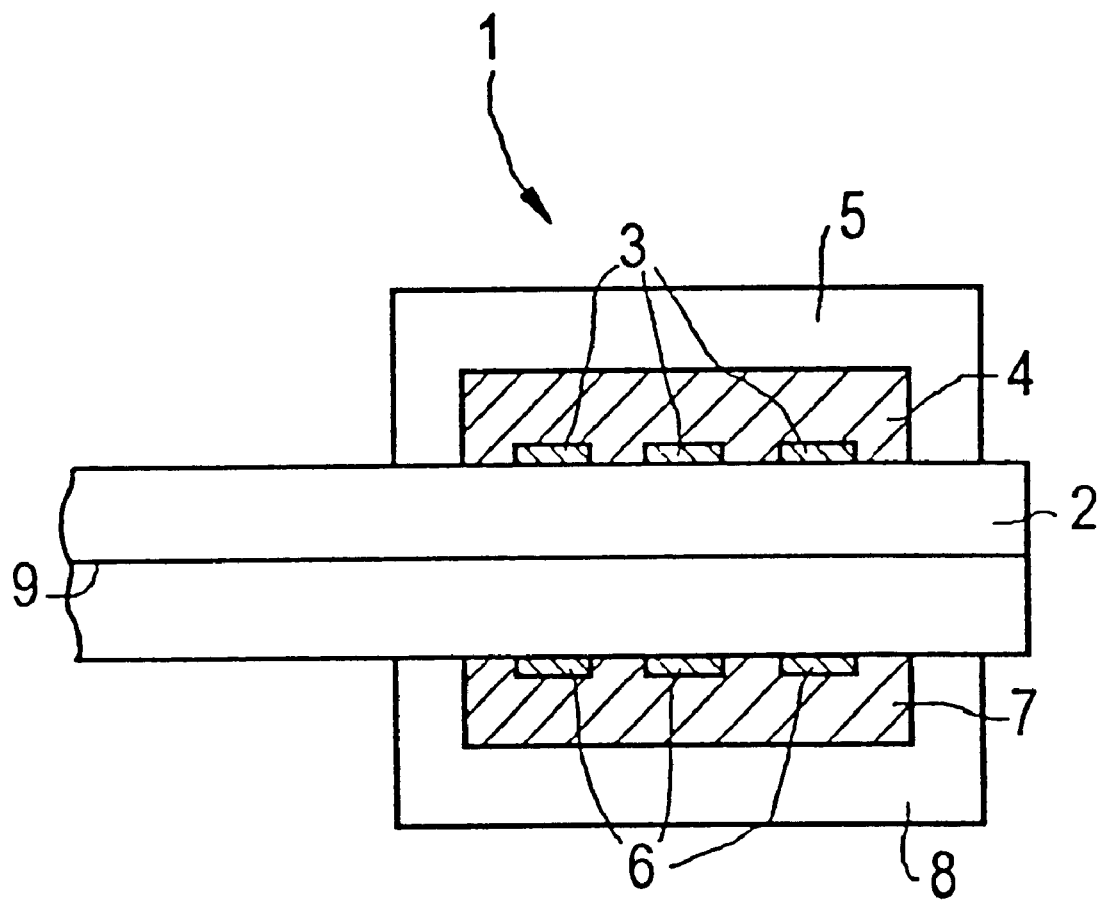

HYDROGEN SENSOR

BACKGROUND OF THE INVENTION

1. Field of the Invention

The present invention relates to a hydrogen sensor having a semiconductor layer which is sensitive to hydrogen as a function of temperature and a covering layer which is selectively permeable to hydrogen.

2. Description of the Prior Art

A general problem of gas sensors is that changes in the measured value are observed even when the gas component to be measured does not change. This is particularly disruptive if one component with a low mixture ratio or low concentration is to be measured in the presence of large but variable concentrations of gases which cause cross-sensitivities.

It has been attempted to develop a hydrogen sensor which uses gallium oxide, $Ga_2O_3$, as the semiconductive metal oxide. This substance also responds to other gases, in particular oxygen and hydrocarbons. For this reason, the sensor has at most a limited suitability for measurements in environments in which the above gas components fluctuate considerably. It has therefore been attempted to arrange a covering layer on top of the gallium oxide, which selectively allows hydrogen to pass through while other components are prevented from gaining access to the gas-sensitive semiconductor layer.

However, even with a covering layer of this type a gallium oxide sensor frequently gives only unsatisfactory results when measuring exhaust gas. This is because, in addition to the presence of interfering gas components of fluctuating composition, other factors also have adverse effects during gas measurement, in particular the measurement of exhaust gas in automobiles. These factors include the fact that electromagnetic interference etc., which may be particularly intensive in the automotive sector, frequently result in very poor measurement of the electrical parameters, such as the electrical conductivity, of the semiconductor layers used. In addition, the variation in other variables, for example the temperature of the sensor used, as a result of fluctuations in the ambient temperature or a drift in the supply of heating energy, may also have adverse effects.

German Patent Document No. 42 03 522 C1 has disclosed an oxygen sensor arrangement based on semiconductive metal oxides in which the temperature sensitivity has been reduced. When the metal oxides are at elevated temperature, the conductivity depends on the oxygen partial pressure, the sensor arrangement having two individual metal oxide sensors which, in the intended measurement area, have conductivities which exhibit different relationships with the oxygen partial pressure but substantially the same relationship with the temperature. The theory is that the temperature dependency is to be substantially taken out in the quotient formed from the conductivity measurement signals from the two sensors.

SUMMARY OF THE INVENTION

The present invention is based on the object of providing a novel arrangement for industrial use, in particular, although not exclusively, of providing a gas sensor which is particularly suitable for measuring hydrogen and can also be used in particular for exhaust gas measurements.

The invention is based on the recognition that strontium titanate, once it has been covered with a covering layer which selectively filters hydrogen, is eminently suitable for use as a hydrogen sensor and that, by way of a suitable different doping of the two layers, it is also possible to compensate for the temperature sensitivity during the measurement of hydrogen. It is assumed that the hydrogen filtering action is brought about by a selective permeability to this substance, although in particular a quasi-selective reaction of hydrogen with oxidizing substances in the covering layer also cannot be ruled out altogether. The precise mechanism of the conductivity change is actually unclear. One possible assumption is that, unlike in the case of oxygen detection using strontium titanate semiconductors, where oxygen is introduced into the crystal lattice in atomic form, where it changes the electronic properties of the lattice, in the present case a reversible chemical reaction takes place between the hydrogen and the materials in the semiconductor, and this reaction can only be detected indirectly as a change in an electrical characteristic. A further supposition is that hydrogen accumulates on the surface of the strontium titanate and as a result changes the electronic band structure of the semiconductor in the vicinity of the surface.

A preferred covering layer will contain silicon as a constituent, which can be attributed to the fact that many silicon compounds have a crystal lattice which is so tight that apart from hydrogen it is impossible for any gases, or at least any relevant gases, to pass through, and another advantage is that many silicon compounds have at most a poor conductivity within the intended temperature range of the sensors, so that the measurements of the electrical parameters of the strontium titanate semiconductor layers are at most slightly, and in practice not significantly, affected. Preferably, the covering layers consist of silicon dioxide and/or silicon nitride. Applying the covering layer as a thin film by sputtering or CVD ensures that the covering layer has a structure which is sufficiently impermeable to interfering gases.

Preferably, one of the strontium titanate layers will be n-doped and the second will be p-doped. The changes in the properties of the strontium titanate caused by hydrogen are reversible and, due to the different dominating electrical conduction mechanisms in the n-doped and p-doped layers, may typically act as opposite changes in the conductivity of the individual layers. Consequently, a reduction in conductivity is observed in one layer and an increase in conductivity is observed in the other layer.

It is preferable for the electrical conductivity of the two semiconductor layers to be measured as a function of the hydrogen concentration and then for the difference or the quotient of the corresponding measured values to be determined as the hydrogen measurement signal.

DESCRIPTION OF THE DRAWINGS

FIG. 1 shows a hydrogen sensor according to the present invention.

DESCRIPTION OF THE PREFERRED EMBODIMENT

According to the figure, a hydrogen sensor, which is denoted overall by 1, comprises a carrier substrate 2 made from electrically insulating material which is able to withstand high temperatures, such as $Al_2O_3$. By way of an interdigital electrode structure 3, a strontium titanate layer 4 is applied to one side of the carrier substrate 2, and this layer is completely covered by a covering layer 5. On the opposite side of the carrier substrate 2, a mirror-symmetrical second interdigital electrode structure 6 is provided, above which there is a second strontium titanate layer 7 which is surrounded on all sides by a covering layer 8.

The carrier substrate 2 may be formed as a high-temperature cofired ceramic (HTTC) structure and in the interior may comprise a temperature sensor arrangement and/or a heating coil arrangement, as jointly indicated in the drawing by the reference numeral 9. Preferably, the heating coil arrangement is provided centrally, in order for the two strontium titanate layers 4 and 7 and/or the two covering layers 5 and 8 to be heated to the same temperature and is designed to generate temperatures of between 800° and 1000° C. therein.

The semiconductive properties of the strontium titanate layers 4 and 7 differ. In one strontium titanate layer, p-type conduction is dominant, while n-type type conduction is dominant in the other. This is achieved by suitable doping and a suitably high concentration of oxygen defects in the strontium titanate. The strontium titanate layer 4 is therefore n-doped, while the strontium titanate layer 7 is p-doped. Suitable doping materials are $Cr^{3+}$ ions for the acceptor doping, since they can substitute $Ti^{4+}$ particularly well due to the identical ionic radii of 61 pm, while $Ta^{5+}$ ions can be used as the donors. The oxygen defect concentration required is achieved by annealing or sintering the layers formed in an atmosphere with oxygen concentrations of at least 1%. The oxygen defect concentration in the strontium titanate is then sufficiently high for the dominant conduction mechanism in one layer to be n-type conduction and in the other layer to be p-type conduction.

The interdigital electrode structures 3 and 6 made from a suitable metal, such as platinum or a platinum alloy, are in electrically conductive contact with corresponding strontium titanate layers and, in order to determine the strontium titanate conductivities, have terminals which can be connected to an evaluation circuit.

The covering layers 5 and 8 are preferably of identical structure and consist of a material which selectively allows hydrogen to pass through. Silicon compounds, such as silicon dioxide or silicon nitride, are particularly suitable.

The gas sensor of the present invention is operated as follows:

The gas sensor is fitted at the site of use, such as a flue-gas duct from an incineration plant, an exhaust pipe from an internal-combustion engine etc., and the heating structure and/or the temperature sensor 9, and the interdigital electrode structures 3 and 6, are connected to suitable wiring. The wiring is designed to provide a current through the heating structure which is used to heat the relevant area of the hydrogen sensor 1 to a temperature of approximately 800° to 1000° C.

The interdigital electrode structures 3 and 6 are connected up in order to measure the electrical conductivity of the strontium titanate layers 4 and 7, respectively.

If the concentration of hydrogen gas in the vicinity of the hydrogen sensor 1 changes, the electrical conductivity of the sensor also changes.

The precise reason for this is not altogether understood. However, it is assumed that a hydrogen gradient forms across the covering layer and hydrogen migrates through the covering layer 5 or 8 in one direction or the other. This may be a result of selective permeability of the covering layer to hydrogen or of the hydrogen reacting with other substances in the covering layer.

In response to this, the electrical conductivity changes in both strontium titanate layers 4 and 7, but in different ways.

The mechanism causing this effect is also not entirely clear. Chemical reactions between the strontium titanate and the hydrogen penetrating into it represent one possible cause; the chemical reactions in turn lead to a change in the oxygen vacancy concentration in the strontium titanate. Then, there is either an increase or decrease in the oxygen in both layers, depending on the change in hydrogen concentration. However, since the production process has provided the two strontium titanate layers with different intrinsic oxygen vacancy concentrations in such a way that in one strontium titanate layer with the given doping the dominant conduction mechanism is p-type conduction and in the other strontium titanate layer with the other doping the dominant conduction mechanism is n-type conduction, the electrical conductivities of the two strontium titanate layers consequently change in opposite ways. While in one strontium titanate layer increasing concentrations of hydrogen result in a fall in conductivity, at the same time the electrical conductivity of the other strontium titanate layer rises. Nevertheless, because the thermal activation energy of the strontium titanate layers is at most slightly affected by the doping, the electrical conductivity of the two layers changes in the same way when the temperature changes.

Another explanation is the accumulation of hydrogen at the surface, which could cause changes in the band structure and also represents an appropriate model for explaining the observed effects.

The conductivity is monitored using the interdigital electrode structures 3 and 6 and is evaluated in an evaluation circuit, where the quotient of the two conductivities is determined. However, since the two conductivities change in different ways as the hydrogen concentration varies, whereas the at least approximately exponential temperature dependency is practically identical for both layers, in particular below 800° C., and scarcely deviates even above this temperature, a substantially temperature-independent measurement of the hydrogen concentration is obtained.

Consequently, it is possible to use the evaluation circuit, by forming a quotient from the electrical conductivities obtained at the two layers, to obtain a high-amplitude, temperature-independent signal.

As an alternative to arranging the two sensor regions opposite one another, they may also be arranged next to one another.

Although modifications and changes may be suggested by those skilled in the art, it is the intention of the inventors to embody within the patent warranted hereon all changes and modifications as reasonably and properly come within the scope of their contribution to the art.

We claim:

1. A hydrogen sensor comprising:
   a carrier substrate and a hydrogen-sensitive semiconductor layer that is applied to said carrier substrate;
   said hydrogen-sensitive semiconductor layer comprising a first and second semiconductor layers that each consist of strontium titanate so as to compensate for temperature fluctuations in said hydrogen-sensitive semiconductor layer, said first semiconductor layer being n-doped and said second semiconductor layer being p-doped; and
   first and second covering layers that cover said respective first and second semiconductor layers so as said first and second covering layers are selectively permeable to an amount of hydrogen.

2. The hydrogen sensor according to claim 1 wherein said first and second covering layers comprise one of silicon and a silicon compound.

3. The hydrogen sensor according to claim 1 wherein said first and second covering layers each are selected from the group consisting of silicon dioxide and silicon nitride.

4. The hydrogen sensor according to claim 2 wherein said first and second covering layers each comprise a thin film.

5. The hydrogen sensor according to claim 1 wherein said first and second covering layers are applied by one of a sputtering and a chemical vapor deposition process.

6. The hydrogen sensor according to claim 1 wherein said first and second semiconductor layers are formed by one of a sintering and annealing process under an oxygen environment.

7. A hydrogen sensor arrangement comprising:
   a hydrogen sensor comprising a carrier substrate and a hydrogen-sensitive semiconductor layer that is applied to said carrier substrate, said hydrogen-sensitive semiconductor layer comprising a first and second semiconductor layer that each consist of strontium titanate so as to compensate for temperature fluctuations in said hydrogen-sensitive semiconductor layer, said first semiconductor layer is n-doped and said second semiconductor layer is p-doped;
   first and second covering layers that cover said respective first and second semiconductor layers so as said first and second covering layers are selectively permeable to an amount of hydrogen; and
   a hydrogen sensor circuit that is connected to said hydrogen sensor for measuring first and said second electrical conductivity of said respective first and second semiconductor layers so as to calculate one of a difference value and a quotient value that corresponds to said first and second electrical conductivity.

8. The hydrogen sensor arrangement according to claim 7 wherein said first and second covering layers comprise one of silicon and a silicon compound.

9. The hydrogen sensor arrangement according to claim 7 wherein said first and second covering layers each are selected from the group consisting of silicon dioxide and silicon nitride.

10. The hydrogen sensor arrangement according to claim 9 wherein said first and second covering layers each comprise a thin film.

11. The hydrogen sensor arrangement according to claim 10 wherein said first and second covering layers are applied by one of a sputtering and a chemical vapor deposition process.

12. The hydrogen sensor arrangement according to claim 7 wherein said first and second semiconductor layers are formed by one of a sintering and annealing process under an oxygen environment.

13. A hydrogen sensor arrangement, comprising:
   a hydrogen sensor having a carrier substrate and a hydrogen-sensitive semiconductor layer that is applied to the carrier substrate, the hydrogen-sensitive semiconductor layer including a first and second semiconductor layer that each include at least strontium titanate so as to compensate for temperature fluctuations in the hydrogen sensitive semiconductor layer, one of the first and second semiconductor layers being n-doped and another of the first and second semiconductor layers being p-doped; and
   first and second covering layers that cover the respective first and second semiconductor layers so as the first and second covering layers are selectively permeable to an amount of hydrogen.

14. A hydrogen sensor arrangement, comprising:
   a hydrogen sensor including a carrier substrate and a hydrogen-sensitive semiconductor layer that is applied to the carrier substrate, the hydrogen-sensitive semiconductor layer including a first and second semiconductor layer that each include at least strontium titanate so as to compensate for temperature fluctuations in the hydrogen-sensitive semiconductor layer, wherein one of the first and second semiconductor layers is n-doped and another of the first and second semiconductor layers is p-doped;
   first and second covering layers that cover the respective first and second semiconductor layers so as the first and second covering layers are selectively permeable to an amount of hydrogen; and
   a hydrogen sensor circuit that is connected to the hydrogen sensor for measuring a electrical conductivity of the first and second semiconductor layers so as to calculate one of a difference value and a quotient value that corresponds to the electrical conductivity of the first and second semiconductor layers.

* * * * *